United States Patent
Stahurski et al.

(10) Patent No.: US 8,075,597 B2
(45) Date of Patent: Dec. 13, 2011

(54) APPARATUS FOR RETAINING VERTEBRAE

(75) Inventors: Terrance Stahurski, Seven Hills, OH (US); C. Michael Nilsson, Cleveland Heights, OH (US)

(73) Assignee: Applied Orthopaedics LLC, Seven Hills, OH (US)

( * ) Notice: Subject to any disclaimer, the term of this patent is extended or adjusted under 35 U.S.C. 154(b) by 694 days.

(21) Appl. No.: 11/233,571

(22) Filed: Sep. 23, 2005

(65) Prior Publication Data

US 2007/0072459 A1   Mar. 29, 2007

(51) Int. Cl.
*A61B 17/70* (2006.01)
(52) U.S. Cl. .................... 606/260; 606/261; 606/278
(58) Field of Classification Search .......... 606/250–253, 606/246, 254, 255, 256, 257, 258, 259, 260, 606/261, 262, 263, 264, 278, 54–59; 439/135–142; 403/398, 399
See application file for complete search history.

(56) References Cited

U.S. PATENT DOCUMENTS

| | | | |
|---|---|---|---|
| 3,862,631 A | 1/1975 | Austin | |
| 4,274,401 A | 6/1981 | Miskew | |
| RE31,809 E * | 1/1985 | Danieletto et al. | 606/57 |
| 4,621,627 A * | 11/1986 | DeBastiani et al. | 606/57 |
| 4,988,349 A * | 1/1991 | Pennig | 606/58 |
| 5,092,867 A * | 3/1992 | Harms et al. | 606/252 |
| 5,176,678 A | 1/1993 | Tsou | |
| 5,201,734 A | 4/1993 | Cozad et al. | |
| 5,246,442 A * | 9/1993 | Ashman et al. | 606/278 |
| 5,344,422 A * | 9/1994 | Frigg | 606/278 |
| 5,366,455 A * | 11/1994 | Dove et al. | 606/250 |
| 5,395,370 A | 3/1995 | Muller et al. | |
| 5,476,464 A | 12/1995 | Metz-Stavenhagen et al. | |
| 5,527,314 A * | 6/1996 | Brumfield et al. | 606/278 |
| 5,534,002 A | 7/1996 | Brumfield et al. | |
| 5,545,167 A | 8/1996 | Lin | |
| 5,562,662 A * | 10/1996 | Brumfield et al. | 606/279 |
| 5,575,792 A | 11/1996 | Errico et al. | |
| 5,609,593 A | 3/1997 | Errico et al. | |
| 5,609,594 A | 3/1997 | Errico et al. | |
| 6,024,745 A * | 2/2000 | Faccioli et al. | 606/54 |
| 6,036,691 A * | 3/2000 | Richardson | 606/57 |
| 6,050,997 A * | 4/2000 | Mullane | 606/250 |
| 6,126,660 A | 10/2000 | Dietz | |
| 6,352,537 B1 | 3/2002 | Strnad | |
| 6,569,164 B1 * | 5/2003 | Assaker et al. | 606/250 |
| 6,656,180 B2 * | 12/2003 | Stahurski | 606/276 |
| 7,479,156 B2 * | 1/2009 | Lourdel et al. | 606/266 |
| 2003/0045874 A1 * | 3/2003 | Thomas, Jr. | 606/61 |
| 2003/0045876 A1 * | 3/2003 | Stahurski | 606/61 |
| 2004/0097933 A1 * | 5/2004 | Lourdel et al. | 606/61 |
| 2005/0234448 A1 * | 10/2005 | McCarthy | 606/57 |
| 2006/0229607 A1 * | 10/2006 | Brumfield | 606/61 |
| 2006/0247631 A1 * | 11/2006 | Ahn et al. | 606/61 |
| 2007/0049933 A1 * | 3/2007 | Ahn et al. | 606/61 |
| 2007/0173819 A1 * | 7/2007 | Sandlin | 606/61 |

FOREIGN PATENT DOCUMENTS

FR   2 817 143 A1   5/2002
JP   2002191614   7/2002

* cited by examiner

*Primary Examiner* — Eduardo C Robert
*Assistant Examiner* — Jan Christopher Merene
(74) *Attorney, Agent, or Firm* — Tarolli, Sundheim, Covell & Tummino LLP (57) ABSTRACT

An apparatus for use in retaining vertebrae of a spinal column in a desired spatial relationship includes a rod which extends along the spinal column and is received in a housing. A connector extends from the housing and engages a vertebra. The connector is movable relative to the housing. An adjusting member is rotatable relative to the housing to move the connector relative to the housing. The adjusting member is accessible from an upper side of the housing.

31 Claims, 8 Drawing Sheets

APPARATUS FOR RETAINING VERTEBRAE

BACKGROUND OF THE INVENTION

The present invention relates to an apparatus for use in retaining vertebrae of a spinal column in a desired spatial relationship.

A known apparatus for retaining vertebrae of a spinal column in a desired spatial relationship includes a longitudinally extending member or rod which extends along the spinal column. A hook is connected with a housing of the apparatus by a pair of fasteners which engage opposite sides of the housing. A portion of a vertebra extends between the hook and the housing. An apparatus having this construction is disclosed in U.S. Pat. No. 6,656,180.

SUMMARY OF THE INVENTION

The present invention provides an improved apparatus for use in retaining vertebrae of a spinal column in a desired spatial relationship. The apparatus includes a housing. The housing has a recess which receives a portion of a rod which extends along the spinal column. A connector extends from the housing and engages a vertebra.

The connector is movable relative to the housing to move a side of the housing and the vertebra relative to each other. An adjusting member is disposed on the housing and is accessible from an upper side of the housing. The adjusting member may be rotatable about an axis which extends through the rod or about an axis which is offset to one side of the rod. Rotation of the adjusting member moves the connector relative to the housing.

The connector may include arm sections which are disposed on opposite sides of the rod. A screw thread convolution on the adjusting member may be disposed in engagement with at least a portion of a screw thread convolution on an arm section of the connector.

The housing may have positioning surfaces to retain the adjusting member against movement along a central axis of the adjusting member while enabling the adjusting member to be rotated about its central axis. The adjusting member may be movable through openings in the housing with a snap action. Alternatively, a clip may be moved into engagement with a portion of the adjusting member with a snap action.

An apparatus constructed in accordance with the present invention has a plurality of features. These features may be utilized together in the manner disclosed herein. Alternatively, these features may be used in various combinations with each other and/or in various combinations with known features of the prior art.

BRIEF DESCRIPTION OF THE DRAWINGS

The foregoing and other features of the present invention will become more apparent upon a consideration of the following description taken in connection with the accompanying drawings wherein.

DESCRIPTION OF SPECIFIC PREFERRED EMBODIMENTS OF THE INVENTION

General Description

An apparatus 20 (FIG. 1) is constructed in accordance with the present invention to retain vertebrae of a spinal column in a desired spatial relationship. The apparatus 20 includes a rod 22 which extends along the spinal column. The rod 22 may be contoured to correspond to a desired contour of the spinal column. The longitudinally extending rod 22 may have a configuration which is different than the illustrated cylindrical configuration. For example, the rod 22 may have a polygonal cross-sectional configuration. If desired, the cross-sectional area of the rod 22 may vary along its length.

The apparatus 20 may be formed of any desired biocompatible material. If desired, the apparatus 20 may be formed of a polymeric material. However, it is believed that it may be desired to form the apparatus of a biocompatible metal. For example, the apparatus 20 may be formed of titanium.

The rod 22 is received in a generally U-shaped recess 24 (FIGS. 1 and 2) formed in a housing 26. A set screw 30 (FIG. 1) has an external thread convolution 32 which engages an internal thread convolution 34 formed in the recess 24 in the housing 26. The set screw 30 cooperates with the housing 26 to press the rod 22 against an arcuate bottom surface 38 of the recess 24. This securely interconnects the housing 26 and rod 22 to hold the housing against movement relative to the rod.

A connector or hook 42 (FIG. 1) extends downward from the housing 38 and engages a vertebra 44. An upper or inner side surface 46 (FIGS. 1, 2 and 3) on the hook 42 engages the vertebra 44 (FIG. 1) to connect the apparatus 20 to the vertebra. The surface 46 may press the vertebra 44 against a lower side surface 48 of the housing 26.

In the illustrated embodiment of the invention, the connector 42 is a hook which engages an inner side surface 50 (FIG. 1) of the vertebra 44. The connector 42 may press an opposite outer side surface 52 on the vertebra 44 against the housing 26. However, it is contemplated that the connector 42 may have a different construction if desired. For example, the connector 42 may penetrate the vertebra 44 rather than engaging the inner side surface 50 of the vertebra. If this is done, the connector 42 may include a screw thread which engages the vertebra 44.

An adjusting member or screw 58 (FIGS. 1-3 and 6) is rotatable relative to the housing 26 to move the hook 42 relative to the housing. A retaining portion 62 (FIGS. 1-4) of the housing 26 cooperates with the adjusting screw 58 to retain the adjusting screw against axial movement relative to the housing during rotation of the adjusting screw.

The adjusting screw 58 engages an internally threaded arm section 64 (FIGS. 1-3 and 5) of the hook 42. The adjusting screw 58 has a head end portion 68 which is engagable by a suitable tool to rotate the adjusting screw 58 and move the hook 42 relative to the housing 26. The adjusting screw 58 is rotatable about an axis which extends along a path of movement of the hook 42 relative to the housing 26.

The head end portion 68 of the adjusting screw 58 and the set screw 30 are both accessible from an upper (as viewed in FIG. 1) side 70 of the housing 26. Since the set screw 30 is accessible from the upper side 70 of the housing 26, the set screw in readily accessible when the apparatus 20 is installed in a human body. The set screw 30 can be loosened to enable the spatial relationship between the rod 22 and housing 26 to be changed.

Figure 1:
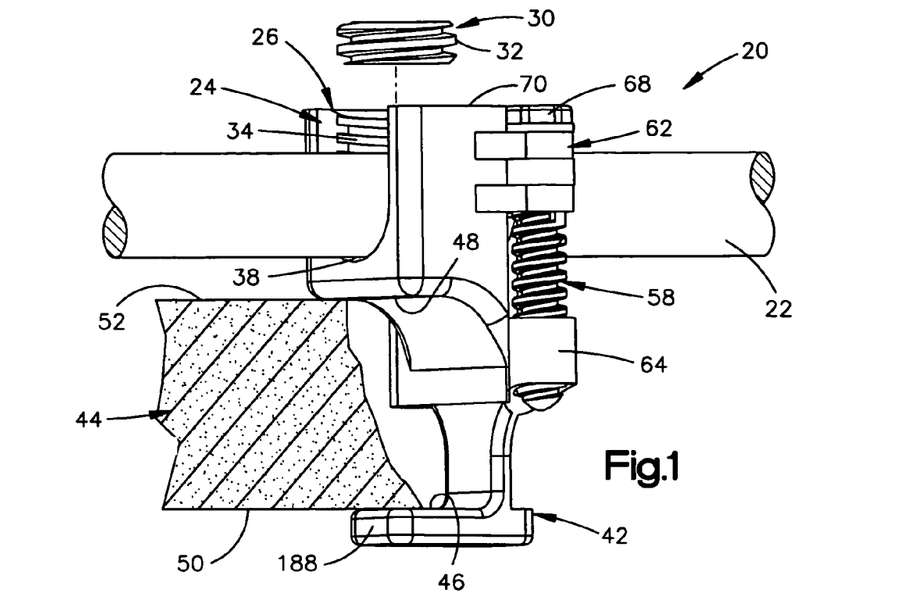
FIG. 1 is a fragmentary schematic pictorial illustration of an apparatus constructed in accordance with the present invention to retain vertebrae of a spinal column in a desired spatial relationship.
Figure 2:
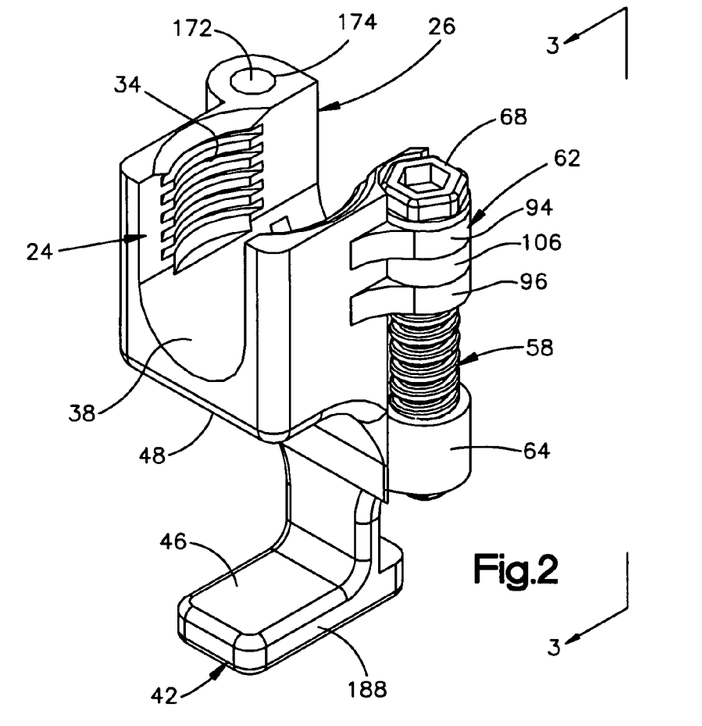
FIG. 2 is a schematic pictorial illustration of a portion of the apparatus of FIG. 1 and illustrating the relationship between a housing, connector member or hook, and an adjusting member which is rotatable to move the connector member relative to the housing.

Since the head end portion 68 of the adjusting screw 58 is also accessible from the upper side 70 of the housing 26 when the apparatus 20 is installed in a human body, the adjusting screw can be actuated to change the spatial relationship between the hook 42 and the housing 26. It is believed that a surgeon will find the accessibility of the set screw 30 and adjusting screw 58 from the upper side 70 of the housing 26 to be particularly advantageous when adjusting the apparatus 20 to obtain a desired spatial relationship between the apparatus and vertebrae of a spinal column. This is especially true when the position of the hook 42 is to be adjusted after the rod 22 has been positioned relative to the housing 26.

Housing

Figures 3, 4:
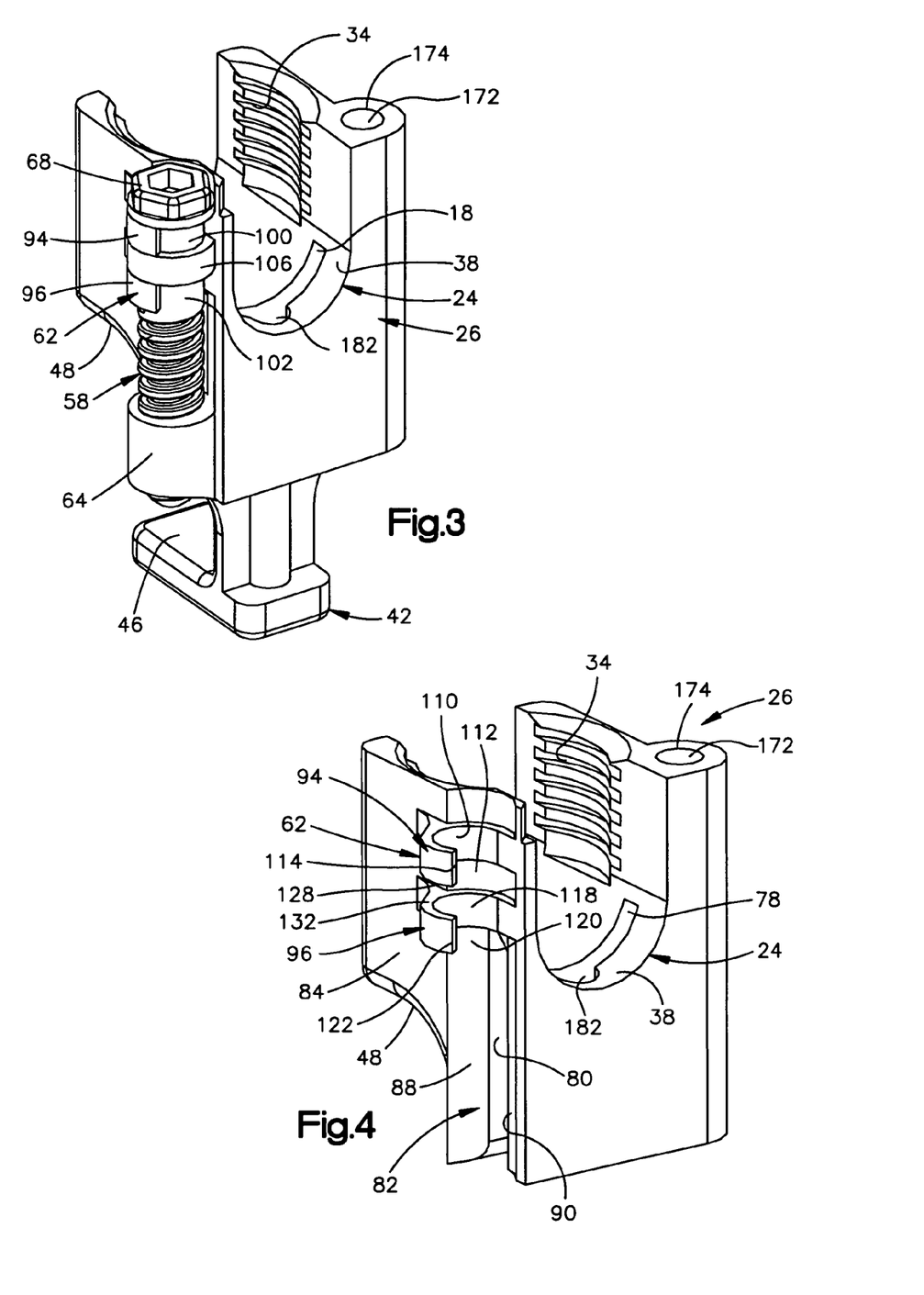
FIG. 3 is a schematic illustration, taken generally along the line 3-3 of FIG. 2, further illustrating the construction of the apparatus.
FIG. 4 is a schematic pictorial illustration of the housing of the apparatus of FIGS. 2 and 3.

The housing 26 grips the rod 22 (FIG. 1) and supports the hook 42. The housing 26 is integrally formed as one piece and includes a slot 78 (FIG. 4) in which the hook 42 (FIG. 5) is slidably received. The slot 78 has a side opening 80 (FIG. 4). The side opening 80 is formed in the bottom of a groove 82 in a side 84 of the housing 26. The groove 82 has arcuate front and rear side surfaces 88 and 90 which engage and rotatably position the adjusting screw 58 (FIG. 3).

The retaining portion 62 of the housing 26 includes a pair of resiliently deflectable retaining arms 94 and 96 which engage cylindrical bearing surfaces 100 and 102 (FIG. 6) on the adjusting screw 58 to rotatably support the adjusting screw (FIG. 3). An annular collar or projection 106 on the adjusting screw 58 is disposed between the bearing surfaces 100 and 102.

The housing 26 (FIG. 4) has an arcuate bearing surface 110 which is disposed on the retaining arm 94 and a side of the housing. The bearing surface 110 is formed as a portion of a cylinder and has an extent of approximately 190 degrees. An opening 112 is formed between an end 114 of the retaining arm 94 and the remainder of the housing 26.

Similarly, an arcuate bearing surface 118 is disposed on the retaining arm 96 and a side of the housing. The bearing surface 118 is formed as a portion of a cylinder and is disposed in a coaxial relationship with the bearing surface 110. The bearing surface 118 has an arcuate extent of approximately 190 degrees. An opening 120 is formed between an end 122 of the retaining arm 96 and the remainder of the housing 26.

The bearing surfaces 110 and 118 are disposed in a coaxial relationship with the arcuate side surfaces 88 and 90 of the groove 82. The retaining arm 94 has a downwardly facing arcuate positioning surface 128 which extends between opposite ends of the opening 112. Similarly, the retaining arm 96 has upwardly facing positioning surface 132 which extends parallel to and faces toward the positioning surface 128 on the retaining arm 94. The positioning surface 132 extends between opposite ends of the opening 120.

The openings 112 and 120 formed between the ends 114 and 122 of the retaining arms 94 and 96 and the remainder of the housing 26 are slightly smaller than the diameter of the bearing surfaces 100 and 102 (FIG. 6) on the adjusting screw 58. The collar 106 (FIG. 6) on the adjusting screw 58 has an axial extent which is the same as the distance between the positioning surfaces 128 and 132 (FIG. 4) on the retaining arms 94 and 96. The collar 106 (FIG. 6) on the adjusting screw 58 has parallel annular side bearing surfaces 140 and 142 which are spaced apart by a distance which is the same as the distance between the positioning surfaces 128 and 132 (FIG. 4) on the retaining arms 94 and 96.

When the adjusting screw 56 (FIG. 6) is to be mounted on the housing 26, the side surfaces 140 and 142 on the collar 106 are aligned with the positioning surfaces 128 and 132 on the retaining arms 94 and 96 (FIG. 4). At this time, the ends 114 and 122 of the retaining arms 94 and 96 are disposed in engagement with the cylindrical bearing surfaces 100 and 102 on the adjusting screw 58. A radially inward force is then applied to the adjusting screw 58 urging the adjusting screw toward the retaining arms 94 and 96.

Figures 5, 6:
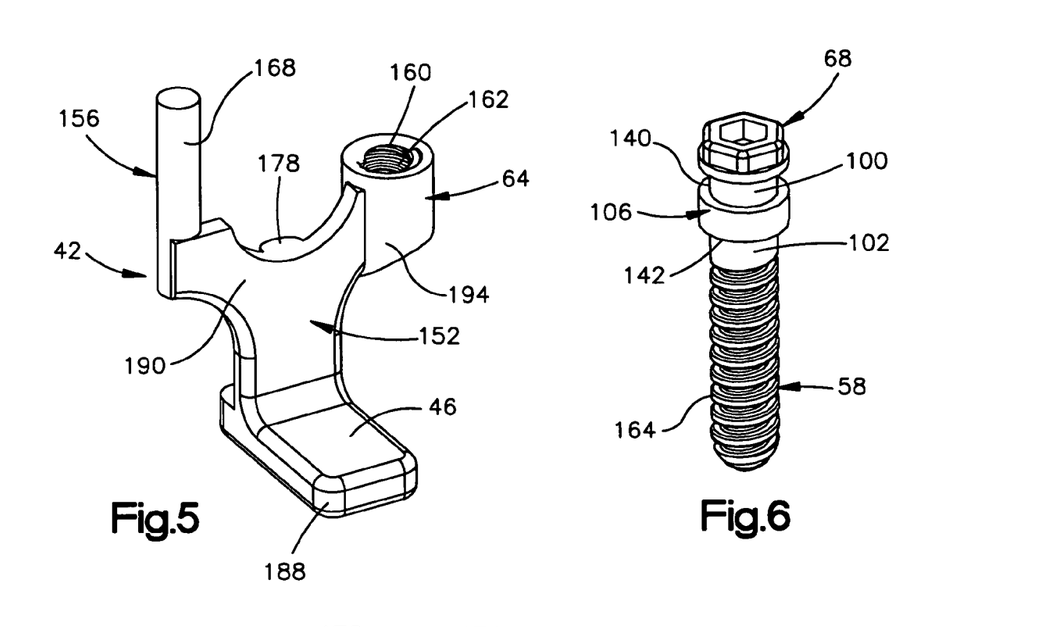
FIG. 5 is a schematic illustration of the connector member which is used in association with the housing of FIG. 4 in the apparatus of FIGS. 2 and 3.
FIG. 6 is an illustration of an adjusting member which is utilized to move the connector member of FIG. 5 relative to the housing of FIG. 4 in the apparatus of FIGS. 2 and 3.

This force results in the retaining arms 94 and 96 being resiliently deflected in a radially outward direction to increase the size of the openings 112 and 120 formed between the retaining arms 94 and 96 and the remainder of the housing 26. The resiliently deflected retaining arms 94 and 96 cause the adjusting screw 58 to move through the openings 112 and 120 with a snap action. As this occurs, the bearing surfaces 100 and 102 on the adjusting screw 58 move into engagement with the bearing surfaces 110 and 118 on the retaining arms 94 and 96.

Figure 10:
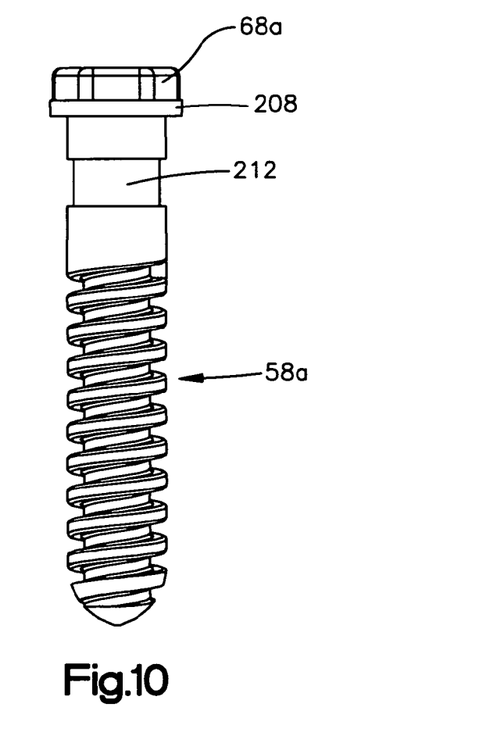
FIG. 10 is an illustration of an adjusting member which is utilized in the apparatus of FIG. 7 to move a connector relative to the housing.

In addition, the side bearing surfaces 140 and 142 on the adjusting screw collar 106 move into engagement with the positioning surfaces 128 and 130 on the retaining arms 94 and 96. Engagement of the side bearing surfaces 140 and 142 on the adjusting screw collar 106 with the positioning surfaces 128 and 132 on the retaining arms 94 and 96 results in the adjusting screw being held against axial movement relative to the housing 26. A central axis of the adjusting screw 58 is offset to one side of the rod 22 (FIG. 10) and extends perpendicular to a central axis of the rod.

Hook

The hook 42 (FIG. 5) engages the vertebra 44 (FIG. 1) to connect the apparatus 20 to the vertebra. The hook 42 is integrally formed as one piece and has a generally L-shaped configuration. The arm section 64 (FIG. 5) extends from one side of the body portion 152 of the hook 42. A second arm section 156 extends from the opposite side of the body portion 152. Central axes of the arm sections 64 and 156 are disposed in a parallel relationship.

The arm section 64 (FIG. 5) of the hook 42 has a generally cylindrical configuration with a central opening 160. The opening 160 has an internal thread convolution 162. The thread convolution 162 engages an external thread convolution 164 (FIG. 6) on the adjusting screw 58.

The arm section 156 has a cylindrical bearing surface 168 (FIG. 5). The bearing surface 168 has a central axis which extends parallel to the central axis of the threaded opening 160 in the arm section 64. Thus, the two arm sections 64 and 156 extend generally parallel to each other.

The body portion 152 of the hook 42 is slidably received in the slot 78 (FIG. 4) in the housing 26. The cylindrical bearing surface 168 on the arm section 156 slidably engages a cylindrical bearing surface 172 (FIG. 4) of an opening 174 in the housing 26. The cylindrical bearing surface 172 has a central axis which extends parallel to the front side surface 88 and rear side surface 90 of the groove 82.

The bearing surface 168 on the arm section 156 (FIG. 5) of the hook 42 cooperates with an arcuate bearing section 178 formed on the body portion 152 of the hook 42 to stabilize the hook as it moves relative to the housing. The bearing section 178 on the hook 42 engages a generally semi-circular bearing portion 182 (FIG. 3) of the slot 78 in the housing 26.

The hook 42 (FIG. 5) has a straight vertebra engaging section 188. The vertebra engaging section 188 of the hook 42 has a flat upper side surface 46 which extends perpendicular to a flat major side surface 190 of the body portion 152. However, it is contemplated that the vertebra engaging section 188 and/or body portion 152 of the hook 42 may have a different configuration if desired. For example, the vertebra engaging section 152 may be configured so that the hook 42 has a generally J-shaped configuration. Alternatively, the vertebra engaging section 188 may be configured to penetrate the vertebra 44 (FIG. 1) rather than engaging the outer side surface 50 of the vertebra.

Assembly and Operation

When the apparatus 20 is to be assembled, the adjusting screw 58 (FIG. 6) is mounted on the housing 26 (FIG. 4) by moving the bearing surfaces 100 and 102 on the adjusting screw through the retaining arm openings 112 and 120 with a snap action. As this occurs, the bearing surfaces 100 and 102 (FIG. 6) on the adjusting screw 58 move into engagement with bearing surfaces 110 and 118 (FIG. 4) on the housing 26. The annular side surfaces 140 and 142 on the collar 106 on the adjusting screw 58 engage the positioning surfaces 128 and 132 on the retaining arms 94 and 96 (FIGS. 4 and 6).

Once the adjusting screw 58 has been positioned on the housing 26, the hook 42 is positioned on the housing 26. To position the hook 42 on the housing 26, the cylindrical bearing surface 168 on the hook arm section 156 (FIG. 5) is moved into engagement with the cylindrical bearing surface 172 of the opening 174 (FIG. 4) in the housing 26. At the same time, the internally threaded opening 160 in the arm section 64 of the hook 42 (FIG. 5) is positioned in the groove 82 (FIG. 4) in the housing 26.

This results in the internally threaded opening 160 in the arm section 64 of the hook 42 being aligned with the lower end portion of the adjusting screw 58. The adjusting screw is then rotated and the hook 42 is moved upwardly (as viewed in FIG. 3) relative to the housing 26. As this occurs, the body portion 152 (FIG. 5) of the hook 42 moves upwardly in the slot 78 (FIGS. 3 and 4) in the housing 26. As the hook 42 is moved upwardly (as viewed in FIG. 3) relative to the housing 26 by rotation of the adjusting screw 58, the adjusting screw is held against axial movement relative to the housing 26 by the cooperation between the collar 106 on the adjusting screw and the retaining arms 94 and 96 on the housing 26.

When the apparatus 20 (FIG. 1) is to be utilized to maintain vertebrae 44 of a spinal column in a desired positional relationship, a surgeon rotates the adjusting screw 58 to provide a desired distance between the upper side surface 46 on the vertebra engaging section 188 of the hook 42 and the lower side surface 48 of the housing 26. Once the housing 26 and hook 42 have been positioned in a desired spatial relationship with a vertebra 44 and the rod 22, the set screw 30 is moved into engagement with the internal threads 44 on the housing 26. The set screw 30 is then tightened to press the rod 22 firmly against the bottom surface 38 of the recess 24 in the housing. The position of the hook 42 can be adjusted even after the rod 22 and the set screw 30 are in place.

Embodiment of FIGS. 7-10

In the embodiment of the invention illustrated in FIGS. 1-6, the adjusting screw 58 is engaged by the retaining arms 94 and 96 with a snap action. In the embodiment of the invention illustrated in FIGS. 7-10, the adjusting screw extends through circular openings in the housing and is engaged by a clip. Since the embodiment of the invention illustrated in FIGS. 7-10 is generally similar to the embodiment of the invention illustrated in FIGS. 1-6, similar numerals will be utilized to designate similar components, the suffix "a" being added to the numerals of FIGS. 7-10 to avoid confusion.

An apparatus 20a (FIG. 7) for use in retaining vertebrae of a spinal column in a desired spatial relationship includes a housing 26a. A rod or elongated member, corresponding to the rod 22 of FIG. 1, is received in a U-shaped recess 24a in the housing 26a. A set screw (not shown) presses the rod against a bottom surface 38a of a recess 24a. The housing 26a is integrally formed of one piece of biocompatible metal, such as titanium.

A connector or hook 42a extends downward (as viewed in FIG. 7) from the housing 26a. The hook 42a has an upper side surface 46a which engages an outer side surface of a vertebra. The surface 46a may press the vertebra against a lower side surface 48a on the housing 26a. The hook 42a is integrally formed as one piece of a biocompatible metal, such as titanium. The hook 42a has the same construction as the hook 42 of FIGS. 1-5.

An adjusting screw 58a (FIG. 7) is disposed in a groove 82a (FIG. 8) having front and rear side surfaces 88a and 90a. The groove 82a has the same general configuration as the groove 82 of FIG. 4.

Figure 7:
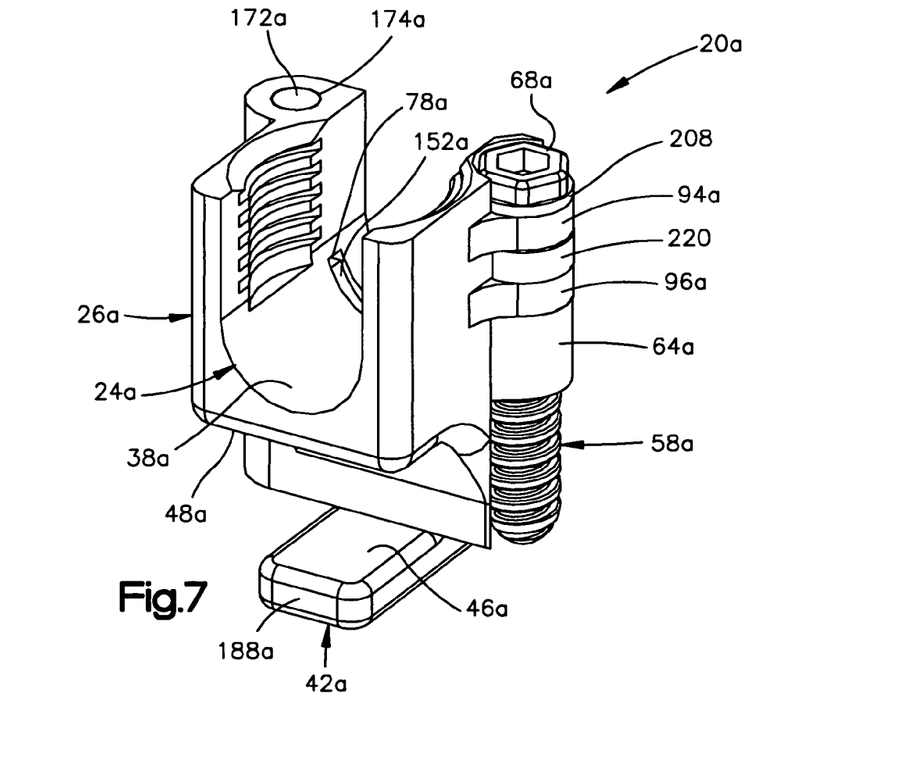
FIG. 7 is a schematic pictorial illustration, generally similar to FIG. 2, of a second embodiment of the apparatus of FIG. 1.
Figure 8:
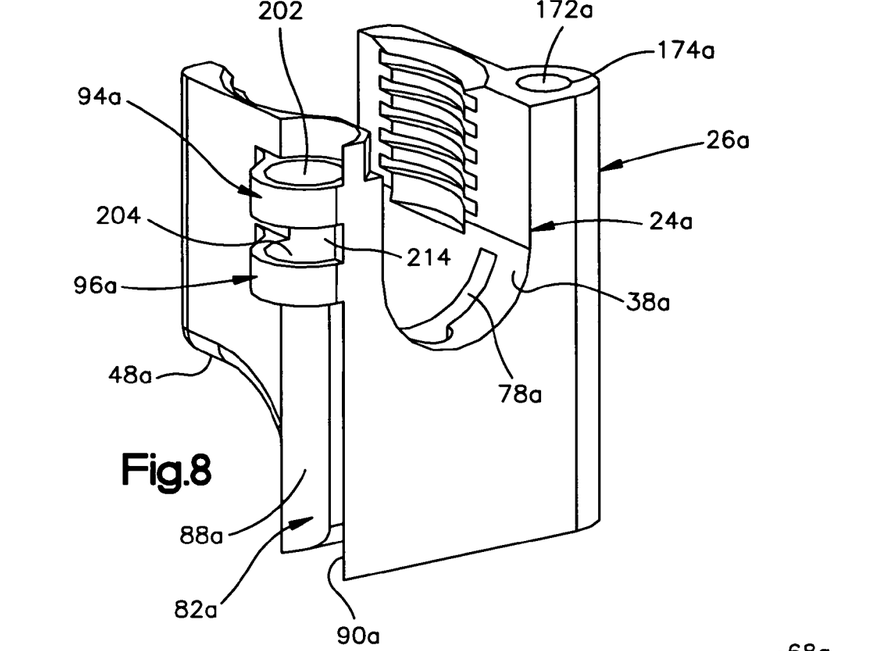
FIG. 8 is a schematic pictorial illustration, generally similar to FIG. 4, illustrating a housing of the apparatus of FIG. 7.

In accordance with one of the features of the embodiment of the invention illustrated in FIGS. 7-10, a pair of retaining arms 94a and 96a (FIGS. 7 and 8) cooperate with the remainder of the housing 26a to form circular openings 202 and 204 (FIG. 8). A head end portion 68a of the adjusting screw 58a has an annular flange 208 (FIG. 10) which engages an upper side surface of the upper retaining arm 94a in the manner illustrated in FIG. 7. This results in an annular groove 212 (FIG. 10) in the adjusting screw 58a being aligned with an opening 214 (FIG. 8) disposed between the upper and lower retaining arms 94a and 96a.

Figure 9:
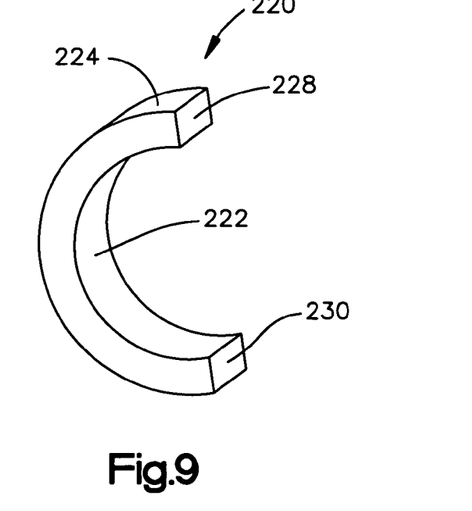
FIG. 9 is a schematic pictorial illustration of a resilient clip which is used in the apparatus of FIG. 7.

The adjusting screw 58a is held against axial movement relative to the housing 26a by a resilient clip 220 (FIG. 9). The clip 220 has coaxial inner and outer side surfaces 222 and 224.

The inner and outer surfaces 222 and 224 have an arcuate extent which is greater than 180 degrees. For example, the clip 220 may have inner and outer side surfaces with an arcuate extent of approximately 190 degrees. The clip 220 is formed of a suitable biocompatible metal, such as titanium, and is resiliently deflectable to increase the distance between opposite end surfaces 228 and 230 on the clip.

Once the adjusting screw 58a has been positioned in the openings 202 and 204 and the groove 88a, the annular groove 212 on the adjusting screw is aligned with the opening 214 between the upper and lower retaining arms 94a and 96a. The clip 220 is then moved into alignment with the opening 214. Opposite ends of the clip are then pressed against the groove 212 in the adjusting screw 58a. This results in the clip being resiliently deflected so that the clip moves into engagement with the adjusting screw 58a with a snap action.

Once the clip 220 has snapped into the groove 212, the clip and adjusting screw are positioned by the retaining arms 94a and 96a in the manner illustrated in FIG. 7. This results in the clip 220 holding the adjusting screw 58a against axial movement relative to the housing 26a.

Once the adjusting screw 58a has been positioned relative to the housing 26a, the hook 42a is moved into a slot 78a in the housing 26a. A bearing surface, corresponding to the bearing surface 168 of FIG. 5, on an arm section, corresponding to the arm section 156 of FIG. 5 of the hook 42a, is disposed in engagement with a bearing surface 172a of a cylindrical opening 174a (FIG. 7) in the housing 26a.

The lower end of the adjusting screw 58a engages an internal thread convolution in an arm section 64a (FIG. 7) of the hook 42a. The adjusting screw is rotatable to move the hook 42a upwardly (as viewed in FIG. 7) relative to the housing 26a. When the hook 42a has moved to the fully retracted position illustrated in FIG. 7, the arm section 64a engages the lower retaining arm 96a. At this time, the body portion 152a (FIG. 7) is disposed adjacent to the upper end portion of the slot 78a in the housing 26a. Of course, the adjusting screw 58a can be rotated to move the upper side surface 46a on the hook 42a away from the lower side surface 48a on the housing 26a.

It should be understood that the hook 42a may have a construction which is different than the construction illustrated in FIG. 7. For example, a vertebra engaging section 188a of the hook 42a may have an arcuate configuration so that the hook 42a has an overall J-shape. Alternatively, the vertebra engaging section 188a may be constructed so as to penetrate a vertebra. If the vertebra engaging section 188a is constructed in such a manner as to penetrate a vertebra, it is believed that it may be desired to provide the vertebra engaging section with a screw type configuration.

Embodiment of FIGS. 11-17

In the embodiments of the invention illustrated in FIGS. 1-10, the adjusting screw 58 is disposed on the outside of the housing 26. In the embodiment of the invention illustrated in FIGS. 11-17, the adjusting screw is disposed within the housing. Since the embodiment of the invention illustrated in FIGS. 11-17 is generally similar to the embodiment of the invention illustrated in FIGS. 1-10, similar numerals will be utilized to designate similar components, the suffix letter "b" being associated with the numerals of FIGS. 11 through 17 to avoid confusion.

An apparatus 20b is utilized to retain vertebrae of a spinal column in a desired spatial relationship. The apparatus includes a longitudinally extending rod 22b (FIG. 11) which extends along a spinal column. It should be understood that although the portion of the rod 22b illustrated schematically in FIG. 11 has a relatively short length, it is contemplated that the rod 22b will be substantially longer and extend along a plurality of vertebrae in a spinal column. Although the illustrated rod 22b has a cylindrical configuration, the rod may have a different configuration if desired. For example, the cross-sectional area of the rod 22b may be different at different locations along the length of the rod.

Figures 11, 12:
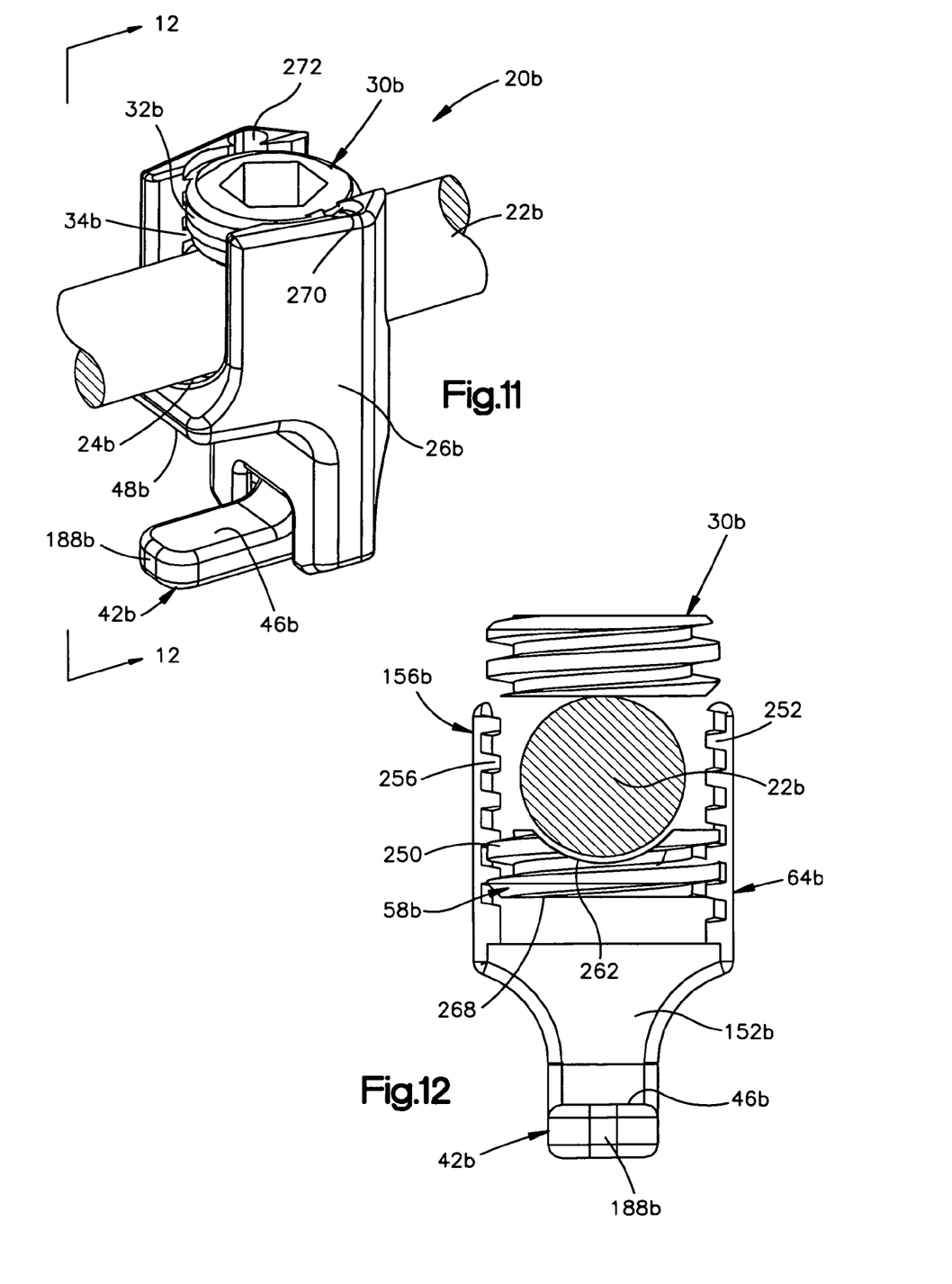
FIG. 11 is a schematic illustration, generally similar to FIG. 1, of a third embodiment of the invention.
FIG. 12 is a schematic pictorial illustration, taken generally along the line of 12-12 of FIG. 11, with a housing of the apparatus removed and illustrating the relationship between an adjusting member and a connector member in the apparatus.

The rod 22b is received in a generally U-shaped recess 24b formed in a housing 26b. A set screw 30b has an external thread convolution 32b which engages an internal thread convolution 34b disposed on the housing 26b in the recess 24b.

A hook or connector 42b extends from the lower side of the housing 26b. The hook 42b has a flat upper side surface 46b that engages a vertebra to connect the apparatus 20b to the vertebra. The surface 46b may cooperate with a lower side surface 48b of the housing 26b to grip the vertebra in the manner illustrated schematically in FIG. 1.

The hook 42b is illustrated in FIG. 12 without the housing 26b. This has been done to clearly illustrate the relationship between the hook 42b and the set screw 30b and adjusting screw 58b.

The set screw 30b (FIG. 12) and adjusting screw 58b are disposed in a coaxial relationship. The coincident central axes of the set screw 30b and adjusting screw 58b extend perpendicular to and intersect the longitudinal central axis of the rod 22b. The adjusting screw 58b has an external thread convolution 250 which engages a portion 252 of a mating internal thread convolution formed on an arm section 64b of the hook 42b. The thread convolution 250 on the adjusting screw 58b also engages a portion 256 of the internal thread convolution disposed on an arm section 156b of the hook 42b. The arm sections 64b and 156b extend parallel to each other and are disposed on opposite sides of a longitudinal central axis of the rod 22b.

The adjusting screw 58b (FIG. 16) has a recess 262 which extends diametrically across the adjusting screw. The recess 262 is engageable with the rod 22b (FIG. 12) to retain the adjusting screw 58b against rotation. However, the recess 262 may be omitted if desired.

Figure 13:
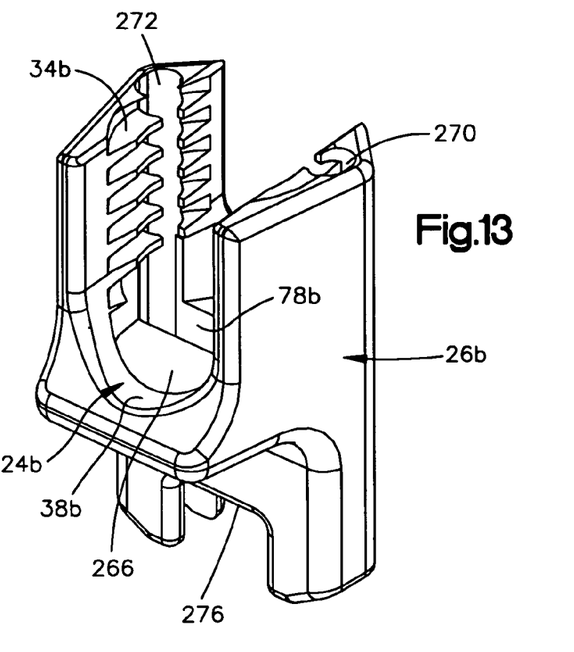
FIG. 13 is a schematic illustration of a housing of the apparatus of FIG. 11.

The recess 38b in the housing 26b has a flat circular bottom surface 266 (FIG. 13). The bottom surface 266 is aligned with a central axis of the housing 26b. The bottom surface 266 is engaged by a flat bottom surface 268 (FIG. 16) of the adjusting screw 58b when the adjusting screw is positioned in the housing 26b.

When the apparatus 20b is to be assembled, the adjusting screw 58b is moved into engagement with the flat bottom surface 266 of the recess 24b. To move the adjusting screw 58b into the recess 24b, the external thread convolution 250 on the adjusting screw 58b is moved into engagement with the internal thread convolution 34b on the inside of the housing 26b. As the adjusting screw 58b is rotated, the adjusting screw moves downward toward the bottom surface 266 (FIG. 13) of the recess 24b in the housing 26b. As this occurs, the external thread convolution 250 on the adjusting screw 58b moves out of engagement with the internal thread convolution 34b on the housing 26b.

Once the external thread convolution 250 on the adjusting screw 58b has moved out of engagement with the internal thread convolution 34b on the housing 26b, the adjusting screw 58b moves into engagement with the flat bottom surface 266 in the housing 26b. The adjusting screw 58b can then be freely rotated relative to the housing 26b without moving axially relative to the housing.

Figure 14:
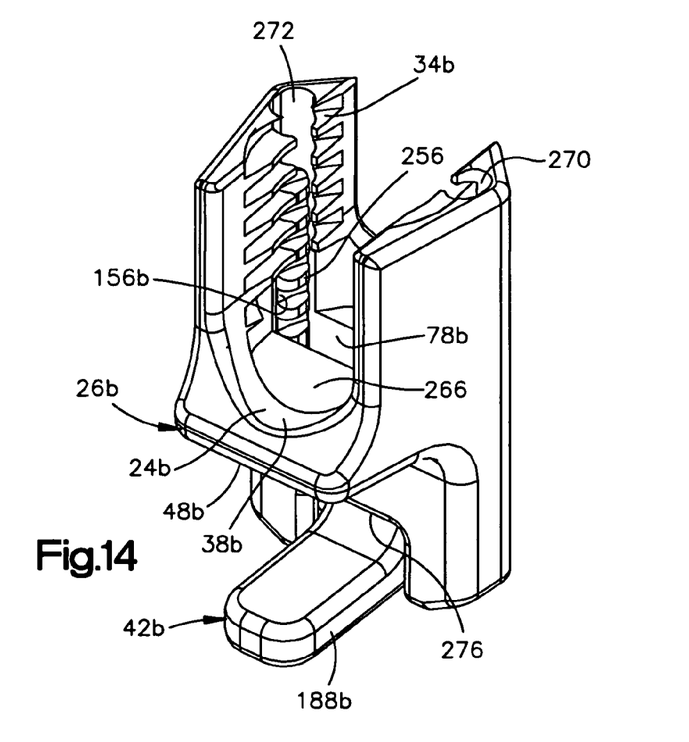
FIG. 14 is a schematic illustration of the housing of FIG. 13 with the connector member positioned in the housing.
Figure 15:
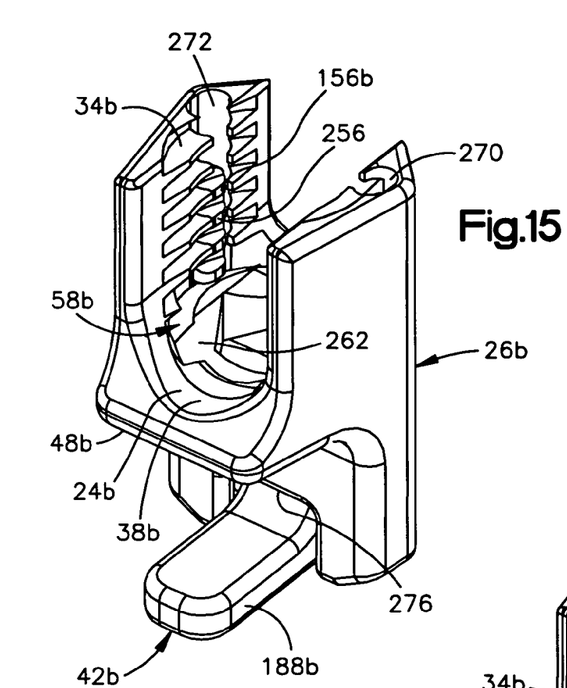
FIG. 15 is a schematic illustration with the adjusting member positioned in the housing of FIG. 14 in engagement with the connector member.
Figure 16:
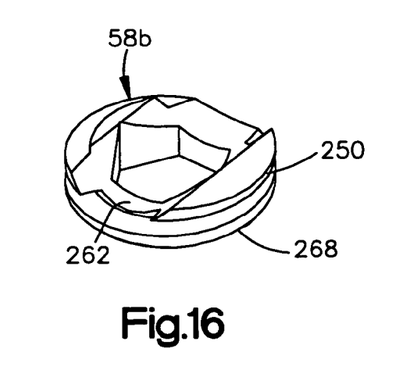
FIG. 16 is a schematic pictorial illustration of the adjusting member of FIG. 15.

The hook 42b is then inserted into the housing 26b in the manner illustrated schematically in FIG. 14. At this time, the arm sections 64b and 156b (FIG. 12) of the hook are disposed in cylindrical grooves 270 and 272 (FIGS. 13 and 14) in the housing 26b. Although only the arm section 156b is illustrated in FIG. 14 as being disposed in the groove 272, it should be understood that the arm section 64b (FIG. 12) is disposed in the groove 270 in the same manner.

The hook 42b has a body portion 152b (FIG. 12) which is received in a slot 78b (FIG. 14) formed in the housing 26b. A vertebra engaging section 188b of the hook 42b may be received in a recess 276 formed in the housing 26b. By providing the recess 276 for the vertebra engaging portion 188b of the hook 42b, the extent of engagement of the arm sections 64b and 156b of the hook 42b with the housing 26b tends to be maximized. This promotes stability of the hook 42b as it is moved downward (as viewed in FIG. 14) from the retracted position illustrated in FIG. 14 to an extended position.

The portions 252 and 256 of the internal thread convolution formed on the arm sections 64b and 156b of the hook 42b move into engagement with the external thread convolution 250 on the adjusting screw 58b. Rotation of the adjusting screw 58b then results in threaded engagement of the thread convolution 250 on the adjusting screw with the portions 252 and 256 of the internal thread convolution 250 on the adjusting screw 58b. The adjusting screw 58b is rotated to move the hook 42b to a position in which the vertebra engaging section 188b of the hook is in a desired spatial relationship with the lower side surface 48b of the housing 26b. The diametrically extending recess 262 (FIG. 16) in the adjusting screw 58b is moved into alignment with the longitudinal axis of the rod 22b when the rod is disposed in the recess 24b (FIG. 11).

Although the adjusting screw 58b has been provided with a recess 262 which cooperates with the rod 22b to hold the adjusting screw against rotation, it is contemplated that the adjusting screw 58b may have a different construction if desired. For example, the adjusting screw 58b may have flat upper and lower side surfaces, in the same manner as does the set screw 30b (FIG. 12). If this is done, a locking device may be provided in association with the adjusting screw 58b. For example, an annular lock washer having tangs which cooperate with recesses in the adjusting screw 58b and the housing 26b may be used to hold the adjusting screw against rotation relative to the housing. Alternatively, a projection on the adjusting screw 58b or a projection on the housing 26b may be deflected to retain the adjusting screw against rotation.

Figure 17:
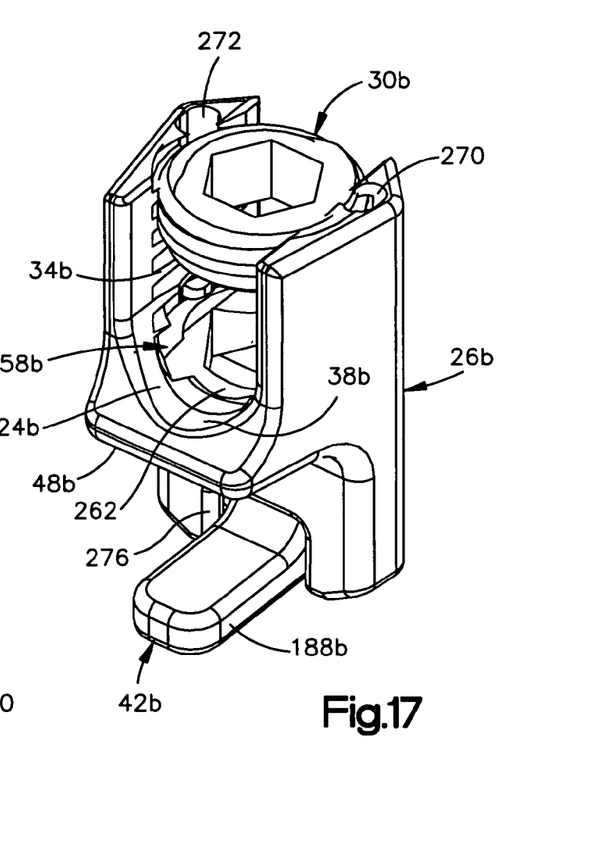
FIG. 17 is a schematic illustration of the apparatus of FIG. 15 with a set screw positioned in the housing.

Once the adjusting screw 58b has been positioned in the housing 26b and the rod 22b positioned in the recess 24b, the set screw 30b is moved into engagement with the threads 34b in the housing 26b (FIG. 17). The set screw 30b is then tightened against the rod 22b to press the rod downward (as viewed in FIG. 11) against the recess 262 in the adjusting screw 58b in the housing 26b. This results in the housing 26b being securely held against movement relative to the rod 22b.

Figure 18:
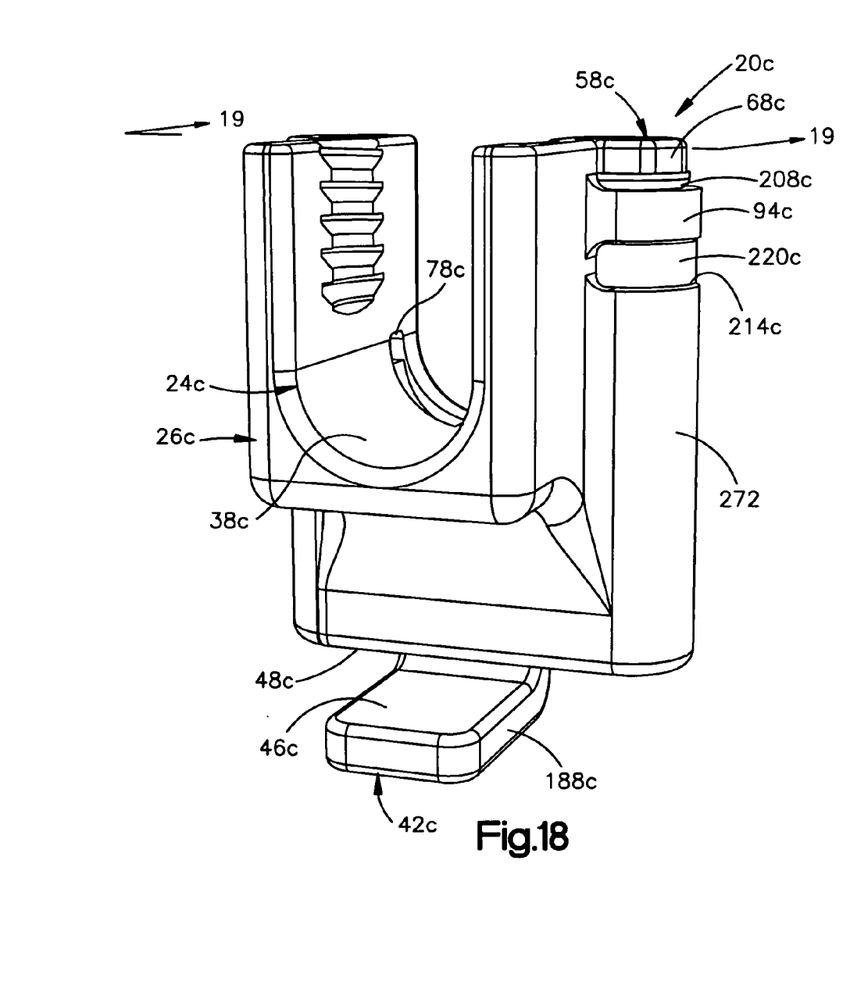
FIG. 18 is a schematic pictorial illustration, generally similar to FIGS. 2 and 7, of a fourth embodiment of the invention.
Figure 19:
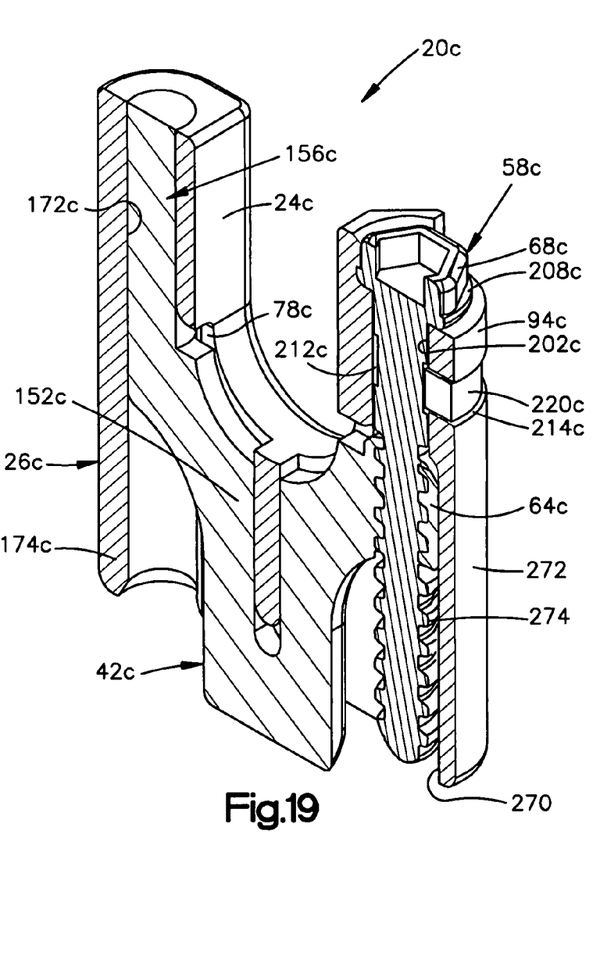
FIG. 19 is a sectional view, taken generally along the line 19-19 of FIG. 18.

Embodiment of FIGS. 18 and 19

In the embodiment of the invention illustrated in FIGS. 7-10, the adjusting screw 58a extends through circular openings 202 and 204 in the housing 26a and is engaged by a clip 220. A threaded portion of the adjusting screw or member 58a (FIG. 7) extends from the arm section 64a of the hook 42a and is exposed to the environment around the apparatus 20a. In the embodiment of the invention illustrated in FIGS. 18 and 19, the threaded portion of the adjusting screw is fully enclosed by the housing. Since the embodiment of the invention illustrated in FIGS. 18 and 19 is generally similar to the embodiments of the invention illustrated in FIGS. 1-10, similar numerals will be utilized to designate similar components, the suffix "c" being added to the numerals of FIGS. 18 and 19 to avoid confusion.

An apparatus 20c (FIG. 18) for use in retaining vertebrae of a spinal column in a desired spatial relationship includes a housing 26c. A rod or elongated member, corresponding to the rod 22 of FIG. 1, is received in a U-shaped recess 24c in the housing 26c. A set screw (not shown), corresponding to the set screw 30 of FIG. 1, presses the rod against a bottom surface 38c of a recess 24c. The housing 26c is integrally formed of one piece of biocompatible metal, such as titanium.

A connector or hook 42c extends downward (as viewed in FIG. 18) from the housing 26c. The hook 42c has an upper side surface 46c which engages a vertebra. The surface 46c may press the vertebra against a lower side surface 48c on the housing 26c. The hook 42c is integrally formed as one piece of a biocompatible metal, such as titanium. The hook 42c has the same construction as the hook 42 of FIGS. 1-5.

In accordance with a feature of this embodiment of the invention, an adjusting screw 58c (FIG. 19) is disposed in a cylindrical passage 270 formed in a sleeve section 272 of the one piece housing 26c. The sleeve section 272 of the housing 26c encloses an external thread convolution 274 on the adjusting screw 58c. Since the thread convolution 274 is fully enclosed by the housing 26c, body tissue and/or a surgeon's glove can not snag on the thread convolution.

A retaining arm 94c cooperates with the sleeve section 272 of the housing 26c to form a circular opening 202c (FIG. 19). A head end portion 68c of the adjusting screw 58c has an annular flange 208c which engages an upper side surface of the upper retaining arm 94c in the manner illustrated in FIG. 18. This results in an annular groove 212c (FIG. 19) in the adjusting screw 58c being aligned with an opening 214c disposed between the upper retaining arm 94c and the sleeve section 272 of the housing 26c.

The adjusting screw 58c is held against axial movement relative to the housing 26c by a resilient clip 220c. The clip 220c has the same construction as the clip 220 of FIG. 9. The clip 220c cooperates with the housing 26c and adjusting screw 58c in the same manner as previously explained in conjunction with the embodiment of the invention illustrated in FIGS. 7-10.

Once the adjusting screw 58c has been positioned in the opening 202c and the passage 270, the annular groove 212c (FIG. 19) on the adjusting screw is aligned with the opening 214c between the retaining arm 94c and the sleeve section 272. The clip 220c is then moved into alignment with the opening 214c. Opposite ends of the clip are then pressed against the groove 212c in the adjusting screw 58c. This results in the clip being resiliently deflected so that the clip moves into engagement with the adjusting screw 58c with a snap action.

Once the clip 220c has snapped into the groove 212c, the clip and adjusting screw 58c are positioned by the retaining arm 94c and sleeve section 272 in the manner illustrated in FIGS. 18 and 19. This results in the clip 220c holding the adjusting screw 58c against axial movement relative to the housing 26c.

Once the adjusting screw 58c has been positioned relative to the housing 26c, the hook 42c is moved into a slot 78c in the housing 26c. A bearing surface 168c (FIG. 19) on an arm section 156c of the hook 42c is disposed in engagement with a bearing surface 172c of a cylindrical opening 174c in the housing 26c.

The adjusting screw 58c engages an internal thread convolution in an arm section 64c (FIG. 19) of the hook 42c. The arm section 64c of the hook 42c is enclosed by the sleeve section 272 of the housing 26c. The adjusting screw 58c is rotatable to move the hook 42c relative to the housing 26c.

When the hook 42c has moved to the fully retracted position illustrated in FIG. 19, the arm section 64c engages the upper end portion of the thread convolution on the adjusting screw 58c. At this time, the body portion 152c of the hook 42c is disposed adjacent to the upper end portion of the slot 78c in the housing 26c. Of course, the adjusting screw 58c can be rotated to move the upper side surface 46c (FIG. 18) on the hook 42c away from the lower side surface 48c on the housing 26c.

It should be understood that the hook 42c may have a construction which is different than the construction illustrated in FIGS. 18 and 19. For example, a vertebra engaging section 188c of the hook 42c may have an arcuate configuration so that the hook 42c has an overall J-shape. Alternatively, the vertebra engaging section 188c may be constructed so as to penetrate a vertebra. If the vertebra engaging section 188c is constructed in such a manner as to penetrate a vertebra, it is believed that it may be desired to provide the vertebra engaging section with a screw type configuration.

CONCLUSION

In view of the foregoing description, it is apparent that the present invention provides an improved apparatus 20 for use in retaining vertebrae of a spinal column in a desired spatial relationship. The apparatus 20 includes a housing 26. The housing 26 has a recess 24 which receives a portion of a rod 22 which extends along the spinal column. A connector 42 extends from the housing 26 and engages a vertebra 44.

The connector 42 is movable relative to the housing 26 to move the connector 42 and the vertebra 44 into engagement. An adjusting member 58 is disposed on the housing 26 and is accessible from an upper side of the housing. The adjusting member 58 may be rotatable about an axis which extends through the rod 22b (FIG. 12) or about an axis which is offset to one side of the rod 22 (FIG. 1). Rotation of the adjusting member 58 moves the connector 42 relative to the housing 26. The connector 42 may include arm sections 64 and 156 which are disposed on opposite sides of the rod 22. A screw thread convolution 164 on the adjusting member 58 may be disposed in engagement with at least a portion of a screw thread convolution 162 disposed on an arm section 64 of the connector 42.

The housing 26 may have positioning surfaces 128 and 132 to retain the adjusting member 58 against movement along a central axis of the adjusting member while enabling the adjusting member to be rotated about its central axis. The adjusting member 58 may be movable through openings 112 and 120 in the housing with a snap action. Alternatively, a clip 220 may be moved into engagement with a portion of the adjusting member 58a with a snap action.

An apparatus constructed in accordance with the present invention has a plurality of features. These features may be utilized together in the manner disclosed herein. Alternatively, these features may be used in various combinations with each other and/or in various combinations with known features of the prior art.

Having described the invention, the following is claimed:

1. An apparatus for use in retaining vertebrae of a spinal column in a desired spatial relationship, said apparatus comprising:

a rod adapted to extend along the spinal column;

a housing having first and second opposite sides, said rod being at least partially disposed between said first and second sides of said housing;

a connector which extends in a first direction from said first side of said housing and is adapted to engage a vertebra, said connector being movable relative to said first and second sides of said housing along a path of movement extending through said first and second sides of said housing; and an adjusting member which rotates relative to said housing to cause said connector to move along said path of movement relative to said first and second sides of said housing and relative to said adjusting member into one of a plurality of positions along said path of movement, said connector being held by said adjusting member in any one of the plurality of positions along the path of movement, said connector being movable into any one of the plurality of positions along said path of movement only while said adjusting member is rotated relative to said housing, said adjusting member rotating about an axis which extends along the path of movement of said connector relative to said housing and being accessible from said second side of said housing, said adjusting member having a portion extending between said first side and said second side.

2. An apparatus as set forth in claim 1 wherein said adjusting member is rotatable about an axis which extends through said rod to move said connector relative to said housing.

3. An apparatus as set forth in claim 1 wherein said adjusting member is rotatable about an axis offset to one side of said rod to move said connector relative to said housing.

4. An apparatus as set forth in claim 1 wherein said connector includes a first arm section which is offset in a first direction from said rod and a second arm section which is offset in a second direction from said rod, said rod being disposed between parallel central axes of said first and second arm sections.

5. An apparatus as set forth in claim 4 wherein said adjusting member includes a screw thread convolution which is disposed in engagement with at least a portion of a screw thread convolution disposed on said first arm section of said connector, said adjusting member being rotatable relative to said housing and first arm section of said connector to move said connector relative to said housing under the influence of force transmitted from said adjusting member to said first arm section of said connector.

6. An apparatus as set forth in claim 5 wherein said second arm section of said connector includes a bearing surface which slides along a bearing surface on said housing to guide movement of said connector relative to said housing during rotation of said adjusting member.

7. An apparatus as set forth in claim 1 wherein said housing includes first and second resiliently deflectable positioning sections which at least partially define first and second openings, said adjusting member being movable through said first and second openings with a snap action by pressing said adjusting member against said positioning sections to resiliently deflect said positioning sections under the influence of force applied against said positioning sections by said adjusting member.

8. An apparatus as set forth in claim 7 further including an annular collar on said adjusting member, said annular collar moves into a space between said positioning sections upon movement of said adjusting member through said first and second openings with a snap action.

9. An apparatus as set forth in claim 1 wherein said housing includes first and second positioning sections which at least partially define first and second openings through which said adjusting member extends, said apparatus further includes a resiliently deflectable clip which is moved into engagement with a portion of said adjusting member with a snap action at a location between said first and second positioning sections.

10. An apparatus as set forth in claim 1 wherein said connector includes a body section which is slidably received in an opening in said housing and an end portion which extends transverse to said body section, said end portion of said connector being engageable with a first surface area on a vertebra, said adjusting member being rotatable relative to said housing to slide said body section of said connector along surfaces which at least partially define the opening in said housing to decrease a distance between said first side of said housing and said end portion of said connector.

11. An apparatus as set forth in claim 1 wherein said adjusting member includes a screw thread convolution that engages a screw thread convolution on said connector such that rotation of said adjusting member relative to said housing causes movement of said connector along said path of movement relative to said first and second sides of said housing and relative to said adjusting member.

12. An apparatus for use in retaining vertebrae of a spinal column in a desired spatial relationship, said apparatus comprising:
a rod adapted to extend along the spinal column;
a housing having first and second opposite sides, said rod being at least partially disposed between said first and second sides of said housing;
a connector which extends in a first direction from said first side of said housing and is adapted to engage a vertebra, said connector being movable relative to said first and second sides of said housing along a path of movement extending through said first and second sides of said housing, said connector including a first arm section which is offset in a first direction from said rod and a second arm section which is offset in a second direction from said rod, said rod being disposed between parallel central axes of said first and second arm sections; and
an adjusting member which is rotatable relative to said housing to move said connector along said path of movement relative to said first and second sides of said housing and said adjusting member into one of a plurality of positions along said path of movement, said connector being held by said adjusting member in any one of the plurality of positions along the path of movement, said connector being movable into any one of the plurality of positions along said path of movement only when said adjusting member is rotated relative to said housing, said adjusting member being rotatable about an axis which extends along the path of movement of said connector relative to said housing and being accessible from said second side of said housing, said adjusting member having a portion extending between said first side and said second side;
wherein said adjusting member includes a screw thread convolution which is disposed in engagement with at least a portion of a screw thread convolution disposed on said first arm section of said connector, said adjusting member being rotatable relative to said housing and first arm section of said connector to move said connector relative to said housing under the influence of force transmitted from said adjusting member to said first arm section of said connector, said screw thread convolution on said adjusting member being disposed in engagement with at least a portion of a screw thread convolution disposed on said second arm section, said adjusting member being rotatable relative to said housing and said first and second arm sections to move said connector relative to said housing under the influence of force transmitted from said adjusting member to said first and second arm sections of said connector.

13. An apparatus for use in retaining vertebrae of a spinal column in a desired spatial relationship, said apparatus comprising:
a rod adapted to extend along the spinal column;
a housing having first and second opposite sides, said rod being at least partially disposed between said first and second sides of said housing;
a connector which extends in a first direction from said first side of said housing and is adapted to engage a vertebra, said connector being movable relative to said first and second sides of said housing along a path of movement extending through said first and second sides of said housing;
an adjusting member which is rotatable relative to said housing to move said connector along said path of movement relative to said first and second sides of said housing and said adjusting member into one of a plurality of positions along said path of movement, said connector being held by said adjusting member in any one of the plurality of positions along the path of movement, said connector being movable into any one of the plurality of positions along said path of movement only when said adjusting member is rotated relative to said housing, said adjusting member being rotatable about an axis which extends along the path of movement of said connector relative to said housing and being accessible from said second side of said housing, said adjusting member having a portion extending between said first side and said second side; and
first and second positioning surfaces disposed in a spaced apart relationship on said housing, and first and second retainer surfaces connected with said adjusting member and disposed in engagement with said positioning surfaces to retain said adjusting member against movement along a central axis of said adjusting member while enabling said adjusting member to be rotated about the central axis of said adjusting member.

14. An apparatus as set forth in claim 13 wherein said retainer surfaces have an annular configuration and are rotatable with said adjusting member.

15. An apparatus as set forth in claim 13 wherein said retainer surfaces are disposed on a clip which engages a groove in said adjusting member, said adjusting member being rotatable relative to said clip during rotation of said adjusting member.

16. An apparatus for use in retaining vertebrae of a spinal column in a desired spatial relationship, said apparatus comprising:
a rod adapted to extend along the spinal column;
a housing having first and second opposite sides, said rod being at least partially disposed between said first and second sides of said housing;
a connector which extends in a first direction from said first side of said housing and is adapted to engage a vertebra, said connector being movable relative to said first and second sides of said housing along a path of movement extending through said first and second sides of said housing; and
an adjusting member which is rotatable relative to said housing to move said connector along said path of movement relative to said first and second sides of said housing and said adjusting member into one of a plurality of positions along said path of movement, said connector being held by said adjusting member in any one of the plurality of positions along the path of movement, said connector being movable into any one of the plurality of positions along said path of movement only when said adjusting member is rotated relative to said housing, said adjusting member being rotatable about an axis which extends along the path of movement of said connector relative to said housing and being accessible from said second side of said housing, said adjusting member having a portion extending between said first side and said second side, wherein said housing includes a third side which extends between said first and second sides, said adjusting member being disposed along said third side of said housing, said housing having a positioning section which at least partially defines an opening through which said adjusting member extends, said connector having an arm section which extends into an opening in said housing, said adjusting member having a thread convolution which engages a portion of a thread convolution on said arm section of said connector.

17. An apparatus for use in retaining vertebrae of a spinal column in a desired relationship, said apparatus comprising:

a rod adapted to extend along the spinal column;

a housing having a recess which extends from an upper side of said housing toward a lower side of said housing and which receives a portion of said rod;

a set screw which is at least partially disposed in said recess in said housing and has a thread convolution which engages at least a portion of a thread convolution formed in opposite sides of said recess in said housing, said set screw cooperates with said housing to urge said rod toward a lower portion of the recess in said housing;

a hook member extending from a lower side of said housing, said hook member includes a body section which is at least partially enclosed by said housing, a vertebra engaging section extending from said body section, and first and second arm sections extending from said body section of said hook member in a direction away from said vertebra engaging section of said hook member; and an adjusting screw which is at least partially enclosed by an adjusting screw retaining portion of said housing, said adjusting screw rotating relative to said housing about a central axis of said adjusting screw and being held during rotation against axial movement relative to said housing along the central axis of said adjusting screw, said adjusting screw has an external thread convolution which engages an internal thread convolution which is connected with said first arm section of said hook member, said external thread convolution on said adjusting screw and said internal thread convolution connected with said first arm section of said hook member cooperating to move said hook member relative to said housing in response to rotation of said adjusting screw relative to said housing, said second arm section of said hook member having a bearing surface which cooperates with said housing to guide movement of said hook member relative to said housing, said adjusting screw and said set screw being accessible from the upper side of said housing to facilitate adjustment of said apparatus.

18. An apparatus as set forth in claim 17 wherein said adjusting screw has an annular bearing section which cooperates with said retaining portion of said housing to retain said adjusting screw against axial movement relative to said housing.

19. An apparatus as set forth in claim 18 wherein said retaining portion of said housing at least partially defines first and second openings through which said adjusting screw extends, said apparatus further includes a resiliently deflectable clip which is moved into engagement with a portion of said adjusting screw with a snap action to engage a portion of said adjusting screw disposed between said first and second openings.

20. An apparatus as set forth in claim 17 further including a clip which engages said adjusting screw and said retaining portion of said housing to retain said adjusting screw against axial movement relative to said housing.

21. An apparatus as set forth in claim 17 wherein said retaining portion of said housing includes first and second sections which at least partially define first and second openings, said adjusting screw being movable through said first and second openings in a direction transverse to the central axis of said adjusting screw with a snap action.

22. An apparatus as set forth in claim 17 wherein said retaining portion of said housing at least partially defines first and second openings through which said adjusting screw extends, said apparatus further includes a resiliently deflectable clip which is moved into engagement with a portion of said adjusting screw with a snap action to engage a portion of said adjusting screw disposed between said first and second openings.

23. An apparatus for use in retaining vertebrae of a spinal column in a desired relationship, said apparatus comprising:

a rod adapted to extend along the spinal column;

a housing having a recess which extends from an upper side of said housing toward a lower side of said housing and which receives a portion of said rod;

a set screw which is at least partially disposed in said recess in said housing and has a thread convolution which engages at least a portion of a thread convolution formed in opposite sides of said recess in said housing, said set screw cooperates with said housing to urge said rod toward a lower portion of the recess in said housing;

a hook member extending from a lower side of said housing, said hook member includes a body section which is at least partially enclosed by said housing, a vertebra engaging section extending from said body section, and first and second arm sections extending from said body section of said hook member in a direction away from said vertebra engaging section of said hook member; and an adjusting screw which is at least partially enclosed by an adjusting screw retaining portion of said housing, said adjusting screw being rotatable relative to said housing about a central axis of said adjusting screw and being held during rotation against axial movement relative to said housing along the central axis of said adjusting screw, said adjusting screw has an external thread convolution which engages an internal thread convolution which is connected with said first arm section of said hook member, said external thread convolution on said adjusting screw and said internal thread convolution connected with said first arm section of said hook member cooperating to move said hook member relative to said housing upon rotation of said adjusting screw relative to said housing, said second arm section of said hook member having a bearing surface which cooperates with said housing to guide movement of said hook member relative to said housing, said adjusting screw and said set screw being accessible from the upper side of said housing to facilitate adjustment of said apparatus;

wherein said adjusting screw has an annular bearing section which cooperates with said retaining portion of said housing to retain said adjusting screw against axial movement relative to said housing, wherein said housing extends around said external thread convolution on said adjusting screw throughout the length of said external thread convolution.

24. An apparatus for use in retaining vertebrae of a spinal column in a desired spatial relationship, said apparatus comprising:
- a rod adapted to extend along the spinal column;
- a housing having first and second sides, said rod being at least partially disposed between said first and second sides of said housing;
- a connector which extends in a first direction from said first side of said housing and is adapted to engage a vertebrae, said connector includes a body section which is at least partially enclosed by said housing, a vertebrae engaging section extending from said body section, and first and second arm sections extending from said body section of said connector in a direction away from said vertebrae engaging section of said connector, a plurality of substantially similar recesses being formed in one of said first and second arm sections; and
- a retainer which directly engages the housing and at least one of the recesses in said one of said arm sections to retain said connector against movement relative to said housing.

25. An apparatus as set forth in claim 24 wherein said retainer is rotatable relative to said housing.

26. An apparatus as set forth in claim 24 wherein said first arm section is offset in a first direction from said rod and said second arm section is offset in a second direction from said rod, said retainer being at least partially disposed between said first and second arm sections.

27. An apparatus as set forth in claim 24 wherein said rod is at least partially disposed between said first and second arm sections of said connector.

28. An apparatus as set forth in claim 24 wherein said plurality of recesses are formed by a thread convolution on one of said first and second arm sections of said connector.

29. An apparatus as set forth in claim 24 wherein the first and second arm sections are formed as one piece with the vertebrae engaging section.

30. An apparatus for use in retaining vertebrae of a spinal column in a desired spatial relationship, said apparatus comprising:
- a rod adapted to extend along the spinal column;
- a housing having first and second sides, said rod being at least partially disposed between said first and second sides of said housing;
- a connector which extends in a first direction from said first side of said housing and is adapted to engage a vertebrae, said connector includes a body section which is at least partially enclosed by said housing, a vertebrae engaging section extending from said body section, and first and second arm sections extending from said body section of said connector in a direction away from said vertebrae engaging section of said connector, wherein a plurality of substantially similar recesses is formed in each of said first and second arm sections of said connector; and
- a retainer which directly engages the housing and at least one of the recesses in said arm sections to retain said connector against movement relative to said housing.

31. An apparatus as set forth in claim 30 wherein the first and second arm sections are formed as one piece with the vertebrae engaging section.

* * * * *